United States Patent [19]

Lorentzen et al.

[11] Patent Number: 5,374,378
[45] Date of Patent: Dec. 20, 1994

[54] FLOWABLE MICROBICIDAL AGENTS

[75] Inventors: Jens-Peter Lorentzen, Cologne; Walter Radt, deceased, Late of Krefeld, By Ingrid Radt, Christian Radt, Volker Radt, heirs; Horst-Dieter Lehmann, Krefeld, all of Germany

[73] Assignee: Bayer Aktiengesellschaft, Leverkusen, Germany

[21] Appl. No.: 6,029

[22] Filed: Jan. 15, 1993

[30] Foreign Application Priority Data

Jan. 25, 1992 [DE] Germany .............................. 4202051

[51] Int. Cl.$^5$ ............................................. A01N 25/02
[52] U.S. Cl. ........................................ 252/380; 422/1; 106/15.05; 428/541
[58] Field of Search ..................... 252/380; 422/1; 428/541; 106/15.05

[56] References Cited

U.S. PATENT DOCUMENTS

| 2,874,087 | 2/1959 | Obladen et al. | 514/737 |
| 3,811,932 | 5/1974 | Hubele | 252/8.8 X |
| 3,932,684 | 1/1976 | Lauermann et al. | 514/736 |
| 4,157,977 | 6/1979 | Dewar et al. | 252/106 |

FOREIGN PATENT DOCUMENTS

| 1021542 | 12/1957 | Germany . |
| 1025102 | 2/1958 | Germany . |
| 802232 | 10/1958 | United Kingdom . |

Primary Examiner—Robert L. Stoll
Assistant Examiner—Valerie Fee
Attorney, Agent, or Firm—Sprung Horn Kramer & Woods

[57] ABSTRACT

There are described liquid microbicidal agents containing compounds from the series comprising o-phenylphenol, p-chloro-m-cresol, p-chloro-m-xylenol and pentachlorophenol and not more than 50 percent by weight of an organic solvent or solvent mixture, and their preparation and use.

10 Claims, No Drawings

FLOWABLE MICROBICIDAL AGENTS

The present application relates to highly-concentrated stable, liquid microbicidal agents their preparation and use.

It is known that the compounds o-phenylphenol (OPP), p-chloro-m-cresol (CMC), p-chloro-m-xylenol and pentachlorophenol have microbicidal properties.

These compounds are distinguished by a broad and rapid action against a large number of bacteria, viruses, moulds and yeasts.

Moreover, particularly advantageous is the fact that there is little interaction of the active compounds with other components of a medium to be preserved, or to be disinfected, which is why the substances are employed in particular for the preservation of industrial products and for disinfection in the hospital and domestic sectors and in animal keeping. Moreover, in particular OPP and CMC have a thoroughly investigated and positive toxicological and ecological profile. These compounds are frequently also used in the above fields of application in the form of a combination since they have a highly complementary spectrum of action from the microbiological point of view. However, since the compounds in question are crystalline substances, it is necessary to add substantial amounts of organic solvents in order to formulate them for use as an industrial preservative or as a disinfectant. The pure substances, however, have a solubility in the usual solvents of up to not more than 50%. In addition, such solutions are frequently disadvantageous in as far as substantial amounts of the active compounds recrystallise out at low temperatures or when nuclei of crystallisation or rough surfaces are present, so that they have to be reconditioned before use. Moreover, the high solvent content is a disadvantage since they can result in incompatibility with the industrial material or with other substances in the disinfection solution. Moreover, a high solvent content in formulations is a disadvantage from the economical, toxicological and ecological points of view.

Surprisingly, it has now been found that highly-concentrated stable liquid microbicidal agents containing at least two compounds from the series comprising o-phenylphenol, p-chloro-m-cresol, p-chloro-m-xylenol and pentachlorophenol as well as not more than 50% by weight of an organic solvent or solvent mixture can be prepared.

It is preferred for two of the abovementioned compounds to be mixed in the ratio 75:25 to 50:50 parts by weight, melted at temperatures from 20° C. to 50° C. and subsequently treated with an organic solvent or solvent mixture.

However, the compounds can also be treated with the organic solvent, or solvent mixture, singly or in the form of a mixture, and dissolved at temperatures up to the melting point of the compounds, or mixtures, in question and, if appropriate, subsequently mixed.

After cooling, stable liquid formulations remain from which the individual compounds no longer recrystallise out in the customary ranges of storage temperatures, even when nuclei of crystallisation or rough surfaces are present and even after standing for several days.

Suitable solvents are preferably polar organic solvents or solvent mixtures. Solvents which are preferably employed in this context are those solvents which contain hydroxyl groups, ester groups, ether groups or mixtures of these functionalities. Esters and glycol derivatives such as ethylene glycol, propylene glycol, diethylene glycol, triethylene glycol and polyethylene glycol may be mentioned by way of example and as being preferred.

The agents according to the invention contain the organic solvent or solvent mixture preferably in amounts from 0 to 30% by weight, in particular 1 to 20% by weight, particularly preferably 5 to 15% by weight.

Very particularly preferred microbicidal agents are those which contain OPP in the form of a mixture with CMC. The mixing ratios of OPP and CMC are here in particular 65 to 55 parts by weight of OPP and 35 to 45 parts by weight of CMC.

In particular the mixture of OPP and CMC have advantages compared with solutions of the pure components with regard to compatibility with the material, solvent expenditure, solvent consumption and solvent pollution. Moreover, it is of particular importance that a mixture of OPP and CMC in the mixing ratios mentioned gives a free-flowing melt at temperatures from as little as 15° C., so that the amount of solvent can be dispensed with completely or, in the case of preparations which must also be liquid below 0° C., kept at a minimum.

Compared to solid formulations such liquid formulations have the advantage of being handled more easily (more easily to transport, dispense and meter due to pumpability) and are dust-free (toxicological advantage, exposure to dust).

The agents according to the invention are advantageously protected against oxidative attack by atmospheric oxygen and against discoloration caused thereby, by using 0.05% to 10% of phosphonobutane-tricarboxylic acid and other oxidation inhibitors.

The agents according to the invention can furthermore be combined with other active compounds to increase the action against bacteria, viruses, moulds and yeasts. The following groups of active compounds may be mentioned by way of example and as being preferred:

1. Phenol derivatives such as, for example, 8-hydroxyquinoline, phenol, cresol, thymols, 2-benzyl-4-chlorophenol as well as derivatives thereof, 2. Aldehydes such as formaldehyde or its depot substances such as, for example, benzyl alcohol mono(-poly)hemiformal, tris-ω-hydroxyethyl-hexahydrotriazine, N-methylolchloroacetamide, dimethylolurea, dimethyloxazolidine, methylenebis-1,3-dimethyloloxazolidine, methylenebis-1,3-oxazine, trisoxymethylmethane, tetrahydro-1,3,5-thiadiazine-2-thione, as well as glutaraldehyde, acrolein, glyoxal, 3. Isothiazolinones such as, for example, 5-chloro-2-methylisothiazolin-3-one, 2-methylisothiazolin-3-one, benzisothiazolinone, N-octylisothiazolinone, cyclopentylisothiazolinone, 4,5-dichloro-N-(octyl or methyl)isothiazolinone, 4. Iodopropargyl alcohol and derivatives such as, for example, iodopropargyl alcohol carbamates $I-C\equiv C-CH_2OCONHR$ where R=H, alkyl, aryl, in particular R=n—$C_4H_9$, Ph. Esters of the iodopropargyl alcohol, in particular with protected or unprotected amino acids, dipeptides and higher peptides, for example $I-C\equiv CCH_2OCH_2OCOCHRNHCO_2C(CH_3)_3$. Ethoxylated iodopropargyl alcohol $I-C\equiv C-CH_2OCH_2CH_2OH$ and its derivatives, triiodoallyl alcohol, 5. Microbistatic or microbicidic alcohols, such as, for example, benzyl alcohol, methanol, ethanol, isopropanol, phenylethyl alcohol, 2-phenoxyethanol, 2- phenoxy-1-propanol, 3-(4-chlorophenoxy)-1,2-propanediol, 2,4-dichlorobenzyl alcohol, 6. Bromonitro compounds such as, for example, 2-bromo-2-nitropropane-1,3-diol or 5-bromo-5-nitro-1,3-dioxane,
7. Organic acids and their derivatives such as, for example, formic acid, acetic acid, chloroacetic acid, bromoacetic acid, peracetic acid, propionic acid, lactic acid, tartaric acid, citric acid, sorbic acid, undecenoic acid, benzoic acid; p-hydroxybenzoic acid and its esters, salicylic acid, dehydroacetic acid, chloroacetamide,
8. 2-Mercaptopyrine 1-oxide, 2-mercaptopyridine and their salts, 2,2'-dithiopyridine 1-oxide,
9. Quaternary ammonium compounds such as, for example, N-alkyl-N,N-dimethyl-benzyl-ammonium chloride, di-n-decyl-dimethyl-ammonium chloride,
10. Guanidine derivatives such as, for example, polyhexamethylene biguanidine hydrochloride, chlorohexidine,
11. Morpholine derivatives such as, for example, 2-(2-nitrobutyl)morpholine or 4,4-(2-ethyl-2-nitrotrimethylene)dimorpholine,
12. Dithiocarbamates such as, for example, salts of dimethyldithiocarbamate,
13. Thiocyanates such as, for example, methylene bis-thiocyanate, 2-thiocyanatomethylthiobenzothiazole.

The agents according to the invention are used for combating bacteria, viruses, moulds and yeast in or on industrial materials, in particular as disinfectants and preservatives.

In particular for disinfection purposes, surface-active substances such as, for example, dodecyl-di(aminoethyl)glycerol, 1-dodecyl-1,4-7-triazaoctane-8-carboxylic acid and salts thereof, amides of coconut propylenediamine such as, for example with glutamic acid, are added to the agents according to the invention. Perfumes as well as other customary additives such as, for example, emulsifiers, stabilisers, corrosion inhibitors and oxidation inhibitors, can furthermore be added.

The following are fields of application for the agents according to the invention:
1. Disinfectants for hospitals, in animal keeping, in the domestic field and the like.
2. Preservation of sizes and glues based on the known animal, vegetable or synthetic raw materials,
3. Preservation of coatings and paints,
4. Preservation of starch products, for example for the printing industry, and of starch solutions, starch dispersions and starch slurries,
5. Preservation of concrete additives for example those based on melasses or ligninsulphonates,
6. Preservation of bitumen emulsions,
7. Preservation of cooling lubricants which can be classified into semisynthetic or fully synthetic emulsions or solutions based on mineral oils.
8. Preservation of polymer dispersions such as, for example, latex dispersions or dispersions based on other polymers,
9. Preservation of slurries such as, for example, for pigments (iron oxide pigments, carbon black pigments, titanium dioxide pigments) or slurries of fillers such as, for example, kaolin, calcium carbonate and the like,
10. Preservation of cleaning agents and detergents for use in industry and in the domestic field,
11. Preservation of other functional fluids such as, for example, humectants for the printing industry,
12. Preservation of mineral oils and mineral oil products.
13. Preservation of auxiliaries for the leather, textile or reproduction industries,
14. Preservation of precursors and intermediates for the chemical industry such as, for example, in the production and storage of dyestuffs,
15. Preservation of writing and drawing inks,
16. Sizes and finishes,
17. Wax and clay emulsion,
18. Starch solutions,
19. Gelatin preparations,
20. Cosmetics.

The examples which follow are intended to illustrate the invention without limiting it thereto. Parts and percentages are parts by weight or percentages by weight.

EXAMPLE 1

40 parts of CMC are combined with 60 parts of OPP at 20° C. and left at this temperature for 5 hours.

A clear, free-flowing melt which does not contain any solids is obtained. A solution which is stable for several weeks at −10° to 50° C. is obtained by adding 10 parts by weight of ethylene glycol.

EXAMPLE 2

35 parts of CMC are combined with 65 parts of OPP at 20° C. and left at this temperature for 5 hours.

A clear, free-flowing melt which does not contain any solids is obtained. A solution which is stable for several weeks at −10° to 50° C. is obtained by adding 10 parts by weight of ethylene glycol.

EXAMPLE 3

45 parts of CMC are combined with 55 parts of OPP at 20° C. and left at this temperature for 5 hours.

A clear, free-flowing melt which does not contain any solids is obtained. A solution which is stable for several weeks at −10° to 50° C. is obtained by adding 5 parts by weight of propylene glycol.

COMPARISON EXAMPLE a) 10 parts of ethylene glycol are added to 100 parts of OPP at 20° C. No solution is obtained, even after stirring at 20° C. for several hours.

b) 10 parts of ethylene glycol are added to 100 parts of CMC at 20° C. No solution is obtained, even after stirring at 20° C. for several hours.

c) As in a) and b), but using propylene glycol. Again, no solution is obtained.

EXAMPLE 4

40 parts of CMC are combined with 60 parts of OPP and 10 parts of ethylene glycol at 20° C. and stirred for 4 hours at this temperature.

A clear solution is obtained from which no solids crystallise out, not even after several weeks.

EXAMPLE 5

In each case 10 parts of ethylene glycol are added to each of 50 parts of CMC and 50 parts of OPP, and the mixtures are stirred at 70° C. until two clear solutions have formed. The two solutions are then combined while hot. After cooling, a stable clear solution remains.

We claim:
1. A highly concentrated microbicidal composition which is liquid at room temperature by weight consisting essentially of 75 to 50% of o-phenylphenol, 25 to 50% of p-chloro-m-cresol, 0 to 30% of an organic solvent and optionally an oxidation inhibitor.

2. A composition according to claim 1, containing at least one polar organic solvent.

3. A composition according to claim 1, containing a glycol derivative as solvent.

4. A composition according to claim 1, containing 1 to 20% by weight of solvent.

5. A composition according to claim 1, wherein the o-phenylphenol is present in from 65 to 55% by weight and the p-chloro-cresol is present in from 35 to 45% by weight.

6. In the combating of bacteria, viruses, molds and yeasts in and on industrial materials applying to such industrial materials an agent suitable therefor, the improvement wherein such agent is a composition according to claim 1.

7. A process for making the composition according to claim 1, which comprises mixing the o-phenylphenol and p-chloro-m-cresol, melting the mixture at about 20° to 50° C., treating the melt with the organic solvent, and bringing the temperature to ambient temperature.

8. A process for making the composition according to claim 1, which comprises mixing the o-phenylphenol and p-chloro-m-cresol, adding to the mixture the organic solvent, heating the mixture plus solvent to form a liquid, and bringing the liquid to ambient temperature.

9. A process for making the composition according to claim 1, which comprises mixing the o-phenylphenol with organic solvent, mixing the p-chloro-m-cresol with organic solvent, heating each of the mixtures to form a single liquid phase, mixing the liquid phases, and bringing the temperature to ambient temperature.

10. A composition according to claim 1, containing 0.05 to 10% of the oxidation inhibitor.

* * * * *